Figure 1:
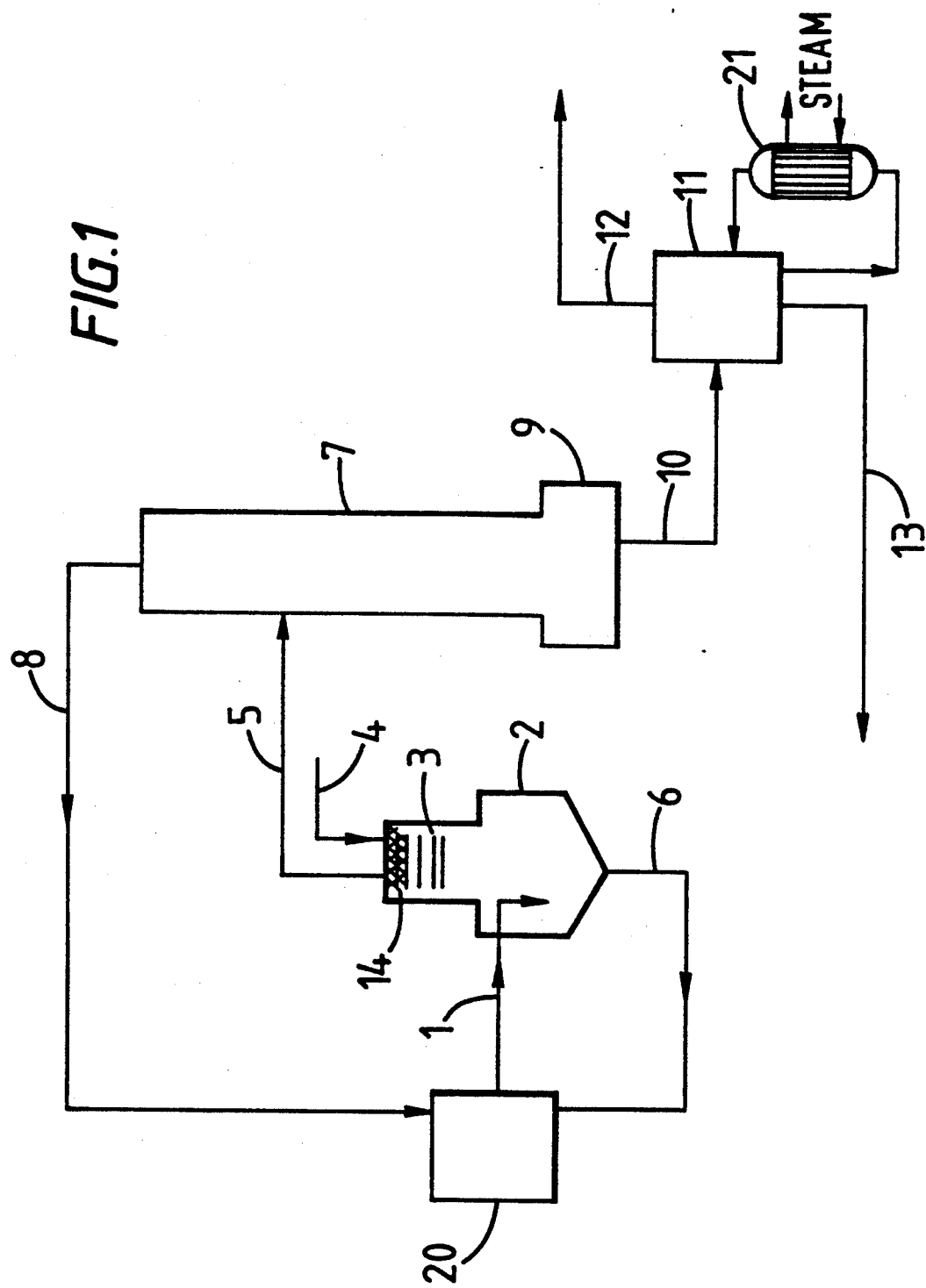

United States Patent [19]

Cooper

[11] Patent Number: 5,227,520
[45] Date of Patent: Jul. 13, 1993

[54] PROCESS FOR THE PURIFICATION OF CARBOXYLIC ACIDS AND/OR THEIR ANYHDRIDES

[75] Inventor: Jeremy B. Cooper, Cuckfield, England

[73] Assignee: BP Chemicals Limited, London, England

[21] Appl. No.: 945,720

[22] Filed: Sep. 16, 1992

[30] Foreign Application Priority Data

Oct. 2, 1991 [GB] United Kingdom ............... 9120902

[51] Int. Cl.$^5$ ...................... C07C 51/12; C07C 53/08
[52] U.S. Cl. ...................... 562/519; 203/71; 203/88
[58] Field of Search ............. 562/519; 203/71, 88

[56] References Cited

U.S. PATENT DOCUMENTS

| | | | |
|---|---|---|---|
| 2,230,112 | 1/1941 | Haney | 260/548 |
| 2,278,831 | 4/1942 | Cockerille | 260/541 |
| 2,352,253 | 6/1944 | Cockerille | 260/546 |
| 2,663,681 | 12/1953 | Hull et al. | 202/40 |
| 3,700,566 | 10/1972 | Bellanger et al. | 203/71 X |
| 3,709,795 | 1/1973 | Singleton | 203/31 |
| 3,769,177 | 10/1973 | Eubanks | 203/71 |
| 3,772,156 | 11/1973 | Johnson | 203/33 |
| 3,791,935 | 2/1974 | Eubanks et al. | 203/74 |
| 4,008,131 | 2/1977 | Price | 203/82 |
| 4,029,553 | 6/1977 | Price | 203/94 |
| 4,039,395 | 8/1977 | Eby | 203/38 |
| 4,039,428 | 8/1977 | Wei | 203/37 |
| 4,107,002 | 8/1978 | Eck et al. | 203/75 |
| 4,549,937 | 10/1985 | Erpenbach et al. | 203/40 |
| 4,650,615 | 3/1987 | Rizkalla | 260/546 |
| 4,664,753 | 5/1987 | Erpenbach et al. | 203/29 |
| 4,792,620 | 12/1988 | Paulik et al. | 560/232 |
| 4,975,155 | 12/1990 | Gracey | 203/38 |
| 5,033,104 | 3/1991 | Paulik et al. | 560/517 |

FOREIGN PATENT DOCUMENTS

| | | |
|---|---|---|
| 0087870 | 7/1983 | European Pat. Off. . |
| 0391680 | 10/1990 | European Pat. Off. . |
| 0479463 | 8/1992 | European Pat. Off. . |
| 49-054324 | 6/1974 | Japan . |
| 50-083315 | 2/1975 | Japan . |
| 50-022532 | 7/1975 | Japan . |
| 54-038082 | 3/1979 | Japan . |
| 54-115313 | 12/1979 | Japan . |
| 58-116436 | 12/1983 | Japan . |
| 850176 | 9/1960 | United Kingdom . |
| 1168121 | 10/1969 | United Kingdom . |
| 1233121 | 5/1971 | United Kingdom . |
| 1294432 | 10/1972 | United Kingdom . |

*Primary Examiner*—Arthur C. Prescott
*Attorney, Agent, or Firm*—Brooks Haidt Haffner & Delahunty

[57] ABSTRACT

A process for purifying an iodide-contaminated carboxylic acid and/or anhydride fraction obtained by liquid phase carbonylation using a carbonylation catalyst, an iodine-containing promoter and optional iodine-containing copromoter comprises vaporizing the fraction after it has been freed of catalyst, feedstock and promoter components to produce a vapor acid and/or anhydride fraction having reduced iodide contamination.

11 Claims, 2 Drawing Sheets

PROCESS FOR THE PURIFICATION OF CARBOXYLIC ACIDS AND/OR THEIR ANYHDRIDES

The present invention relates generally to the purification of carboxylic acids and/or their anhydrides and in particular to the removal of iodide impurities from carboxylic acids and/or their anhydrides produced by the liquid phase carbonylation of lower alcohols and/or their esters using iodine-containing promoters, preferably from acetic acid and/or acetic anhydride produced by the liquid phase carbonylation of methanol and/or methyl acetate.

Acetic acid and acetic anhydride have been known as industrial chemicals for many years. Acetic anhydride constitutes the second largest end use for acetic acid and is widely employed in the production of cellulose acetate and other cellulose esters. Smaller quantities are used in the production of specialist esters, aspirin and pesticides. Acetic acid is used as a preservative and as an intermediate in the production of, for example, acetate esters.

The production of acetic acid by the liquid phase carbonylation of methanol is a well-known industrially operated process and is widely operated commercially. The carbonylation process, which is typically catalysed by rhodium and methyl iodide, is described in detail in, for example, GB 1233121. European patent application number EP-A-0087870 describes a modification in which acetic anhydride, with or without the net co-production of acetic acid, is obtained from methanol and carbon monoxide in a series of esterification, carbonylation and separation, steps. In more detail the latter process comprises:

(1) reacting methanol with recycle acetic acid in an esterification step to form an esterification product containing predominantly methyl acetate, water and optionally unreacted methanol, (2) removing part of the water from the esterification product, (3) reacting the esterification product still containing water with carbon monoxide in a carbonylation step in the presence as catalyst of free or combined metallic carbonylation catalyst and, as promoter, free or combined halogen to form a carbonylation product containing acetic acid and acetic anhydride, (4) separating the carbonylation product by fractional distillation into a low boiling fraction containing carbonylation feed and volatile carbonylation promoter components, acetic acid and acetic anhydride fractions, and a higher boiling fraction containing carbonylation catalyst components, (5) recycling the low boiling fraction containing carbonylation feed and carbonylation promoter components and the higher boiling fraction containing carbonylation catalyst components to the carbonylation step, and (6) recycling at least part of the acetic acid fraction to the esterification step.

The production of carboxylic acid anhydrides by carbonylation is described for example in U.S. Pat. No. 4,792,620 and U.S. Pat. No. 5,003,104.

In liquid phase carbonylation processes, for example that of GB 1,233,121, EP-A-0087870, U.S. Pat. No. 5,003,104 and U.S. Pat. No. 4,792,620 a preferred promoter is an iodine-containing compound, preferably an organo-iodide, such as an alkyl, or aryl halide, methyl iodide being particularly preferred. Also iodide containing co-promoters may be used such as quaternary heterocyclic amine iodide salts as described in EP-A-0391680; alkylated imidazolium iodides as described in EP-A-0479463 and lithium iodide as described in U.S. Pat. No. 4,003,104.

The carbonylation product comprising carboxylic acid and/or anhydride, carbonylation feed, carbonylation catalyst and iodine-containing promoter and optional iodide-containing co-promoter components can be separated by passing to a first distillation column wherein an overhead fraction containing carbonylation feed and iodine-containing promoter components, an intermediate fraction containing carboxylic acid and/or anhydride and a lower fraction containing catalyst and optional co-promoter components are separated, the overhead fraction and the lower fraction being recycled to the carbonylation step, the intermediate fraction being separated, if necessary, by fractional distillation in a second distillation column into a carboxylic acid fraction and a carboxylic acid anhydride fraction.

A problem with carboxylic acids and/or their anhydrides produced by the aforesaid carbonylation processes involving iodine-containing promoters and optional iodine-containing co-promoters is that even after separation and purification as aforesaid they can still contain significant amounts of iodide impurities. For certain applications, for example in the subsequent conversion of acetic acid into vinyl acetate, iodide impurities are detrimental and their removal is highly desirable.

The problem can be alleviated to some extent by feeding the carbonylation product first of all to a flash vapouriser wherein a liquid fraction comprising carbonylation catalyst and optional iodine-containing co-promoters is separated from a vapour fraction comprising carboxylic acid and/or anhydride, carbonylation feed and iodine-containing promoter components, the liquid fraction being recycled to the carbonylation reactor and the vapour fraction being passed to the first distillation column modified to separate only an overhead fraction comprising carbonylation feed and iodine-containing promoter and a lower fraction containing carboxylic acid and/or anhydride. However, the acid and/or anhydride still contains an amount of iodide impurities which is unacceptable for many purposes.

We have now found that he problem of iodide contamination can be substantially reduced by subjecting an iodide-contaminated carboxylic acid and/or anhydride fraction obtained by liquid phase carbonylation using iodine-containing promoters and optional iodine-containing co-promoters, and freed from carbonylation catalyst, carbonylation feed and iodine-containing promoter components and optional iodine-containing co-promoters, to a vapourisation wherein carboxylic acid and/or anhydride having reduced iodide contamination is separated as a vapour fraction from a liquid fraction.

Accordingly, the present invention provides a process for purifying an iodide-contaminated carboxylic acid and/or anhydride fraction obtained by liquid phase carbonylation of a carbonylatable feedstock using a carbonylation catalyst, an iodine-containing promoter and optional iodine-containing co-promoter and freed from carbonylation catalyst, carbonylation feedstock and iodine-containing promoter and optional iodine-containing co-promoter components wherein the iodide-contaminated carboxylic acid and/or anhydride fraction is fed to a vapouriser, hereinafter to be referred to as the post-flash vapouriser, wherein carboxylic acid and/or anhydride having reduced iodide contamination is separated as a vapour fraction from a liquid fraction.

The carboxylic acid and/or anhydride may be $C_2$ to $C_4$ carboxylic acid and/or an anhydride thereof, preferably either acetic acid or acetic anhydride or a mixture thereof.

The iodide-contaminated carboxylic acid and/or anhydride is obtained by liquid phase carbonylation of a carbonylatable feedstock using a carbonylation catalyst, an iodine-containing promoter and optional iodine-containing co-promoter. Further details of the carbonylation, catalysts, promoters and optional iodine-containing co-promoters therefore may be found in the aforesaid patent publications GS 1233121, EP-A-0087870, U.S. Pat. No. 4,792,620 and U.S. Pat. No. 5,003,104, the contents of which are incorporated herein by reference.

Suitable carbonylatable feedstocks comprise alcohols, ethers and/or esters for example methanol, diethyl ether and methyl acetate. The carbonylation catalyst may suitably include the metals of Group VIII of the Periodic Table of the Elements of which the noble metals iridium, osmium, platinum, palladium, rhodium and ruthenium are preferred. Particularly preferred is rhodium. As iodide-containing promoter there may be used elemental iodine, hydrogen iodide, an inorganic iodide salt such as for example sodium, potassium, lithium or cobalt iodide and the like and quaternary ammonium or phosphonium iodide.

Particularly preferred are organic iodides such as alkyl or aryl iodides most preferably methyl iodide. As iodine-containing co-promoter there may be used lithium, magnesium, calcium, titanium, chromium, iron, nickel, and aluminum iodides, most preferably lithium iodide or there may be used quaternary ammonium or phosphonium iodides such as for example N,N'methyl imidazolium iodide or precursors thereof. The use of suitable co-promoters is described in EP-A-0,087,870; EP-A-0,391,680; EP-A-0,479,463 and U.S. Pat. No. 5,003,104 the contents of which are hereby incorporated by reference. Thus EP-A-0,391,680 describes the preparation of carboxylic acids by carbonylation using a co-promoter selected from the group consisting of quaternary ammonium iodides having the formula:

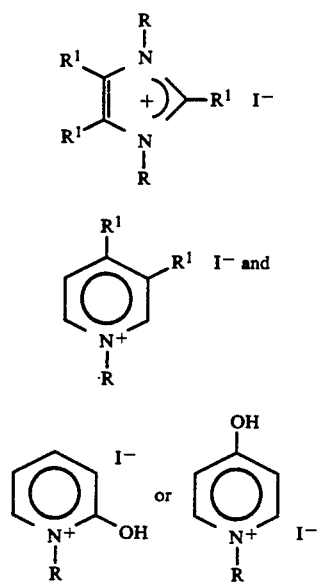

wherein the R and $R^1$ groups are independently selected from hydrogen or $C_1$ to $C_{20}$ alkyl groups with the proviso that at least $R^1$ is other than hydrogen.

EP-A-0,479,463 describes the preparation of carboxylic anhydrides suing a co-promoter selected from the group consisting of:

1,3-dialkyl-4-methylimidazolium iodide;
1,3-dialkyl-4-ethylimidazolium iodide;
1,3-dialkyl-4-n-propylimidazolium iodide:
1,3-dialkyl-4-isopropylimidazolium iodide;
1,3-dialkyl-4n-butylimidazolium iodide;
1,3-dialkyl-4-sec-butylimidazolium iodide;
1,3-dialkyl-4-tert-butylimidazolium iodide;
1,3-dialkyl-2,4,5-trimethylimidazolium iodide and mixtures thereof where the alkyl groups are independently $C_1$ to $C_{20}$ alkyl.

U.S. Pat. No. 5,003,104 describes the carbonylation of methyl acetate in the presence of lithium iodide co-promoter.

Preferably the post-flash vapouriser is a flash vapouriser without fractionation. The temperature, pressure and other operating parameters of the post-flash vapouriser, such as split of liquid to vapour fractions and residence time will depend upon such parameters as the composition, temperature, pressure and flow rate of the iodide-contaminated carboxylic acid and/or anhydride fraction fed to the post-flash vapouriser. Suitably the post-flash vapouriser may be operated at a pressure of up to 10 barg, preferably in the range 0 to 1.5 barg and/or at a temperature in the range 100° to 200° C., preferably 120° to 160° C. Suitably the post-flash vapouriser may be operated with a mass ratio of vapour fraction to liquid fraction in the range 0.5 to 100:1 preferably 5:1 to 30:1. The post-flash vapouriser may be operated on stand-by by not taking any liquid fraction and recycling all of the vapour fraction as feed. Suitably the residence time of liquid in the post-flash vapouriser calculated as the mass of liquid in the post-flash vapouriser divided by the mass feed rate may be up to 60 minutes, preferably in the range 5 to 40 minutes.

Heat may be supplied to the post-flash vapouriser by any suitable means but preferably by steam for example by means of an external thermosyphon reboiler with steam shell-side and process fluid tube-side which takes liquid from the base of the vapouriser and returns liquid-vapour above the liquid level in the vapouriser.

It is preferred that the caroxylic acid and/or anhydride by freed from carbonylation catalyst, carbonylation feed and iodine-containing promoter and optional iodine-containing co-promoter components by feeding the carbonylation product to a preliminary flash vapouriser wherein a liquid fraction comprising carbonylation catalyst and optional iodine-containing co-promoter is separated from a vapour fraction comprising carboxylic acid and/or anhydride, carbonylation feedstack and iodine-containing promoter components, the liquid fraction being recycled to the carbonylation reaction and the vapour fraction being passed to a distillation column wherein an overhead fraction comprising carbonylation feedstock and iodine-containing promoter is separated from a bottoms fraction comprising the iodide-contaminated carboxylic acid and/or anhydride.

The iodide-contaminated acid and/or anhydride bottoms fraction is then passed to the post-flash vapouriser wherein carboxylic acid and/or anhydride having reduced iodide contamination is separated as a vapour fraction from a liquid fraction.

In a modification of this embodiment of the process of the present invention the post-flash vapouriser is integral with the distillation column. Thus the kettle of the distillation column acts as the vapouriser vessel and vapourisation is effected by the distillation column reboiler rather than a separate heat source. Thus in this embodiment an overhead fraction comprising carbonylation feedstock and iodine-containing promoter is removed from the distillation column. A vapour fraction comprising carboxylic acid and/or anhydride is taken as a vapour fraction from the base of the distillation column. This has a lower iodide content than if a liquid fraction were taken from the base of the distillation column. A base liquid fraction is removed separately from the vapour fraction from the base of the distillation column. In this embodiment the vapour fraction may be removed from immediately above the liquid in the kettle at the base of the distillation column or may be removed about one or two trays from the base of the distillation column to prevent entrainment of liquid. Methods known in the art to reduce entrainment may be used.

It is further preferred that the preliminary flash vapouriser be provided in the upper region thereof with a scrubbing section having mesh, sprays, trays or the like and that a liquid, suitably the solvent used to dissolve the catalyst be introduced to the vapouriser above the scrubbing section as wash therefore. Alternatively, or in addition, the upper regions of the preliminary flash vapouriser may be packed with a distillation aid, for example knitmesh. A preferred wash for the scrubbing section in the preliminary flash vapouriser is liquid fraction separated from the post-flash vapouriser.

In our experience acetic acid and acetic anhydride, for example, still contain amounts of iodide impurities in excess of those desirable for certain applications, even when a preliminary flash vapouriser equipped with scrubbing facilities and knitmesh packing is employed in the absence of the post-flash vapouriser. This is particularly the case when iodine-containing co-promoters are used in the carbonylation process. The reason for this can only be a matter for speculation, perhaps very high boiling iodides are entrained in the flash distillate as a very fine mist and/or chemical transformations in the subsequent distillation column produce iodides. Whatever the reason, the fact is that the product can be contaminated with iodide even after the aforesaid procedures. In view of the history of the iodide-contaminated acid and/or anhydride, it is extremely surprising therefore that subjecting the product to an additional flash vapourisation significantly reduces the iodide contamination.

In a particularly preferred embodiment the invention provides a process for the production of acetic anhydride with or without the net co-production of acetic acid from methanol and carbon monoxide in a series of esterification, carbonylation and separation steps comprising:

(1) reacting methanol with recycle acetic acid in an esterification step to form an esterification product containing predominantly methyl acetate, water and optionally unreacted methanol, (2) removing part of the water from the esterification product, (3) reacting the esterification product still containing water as carbonylatable feedstock with carbon monoxide in a carbonylation step in the presence as catalyst of free or combined metallic carbonylation catalyst, an iodine-containing promoter and optionally an iodine-containing co-promoter to form a carbonylation product containing acetic acid and acetic anhydride, (4) feeding the carbonylation product to a preliminary flash vapouriser provided in the upper region thereof with a scrubbing section wherein a liquid fraction comprising carbonylation catalyst and optional iodine-containing co-promoter is separated from a vapour fraction comprising acetic acid, acetic anhydride, carbonylation feedstock and iodine-containing promoter, (5) recycling liquid fraction from (4) to the carbonylation step, (6) separating the vapour fraction from (4) by fractional distillation in a distillation column into a base fraction comprising iodide-contaminated acetic acid and acetic anhydride and an overhead fraction comprising unreacted carbonylation feedstock and iodine-containing promoter, (7) recycling the overhead fraction from (6) to the carbonylation step, (8) feeding the base fraction from (6) comprising iodide-contaminated acetic acid and acetic anhydride to a post-flash vapouriser wherein acetic acid and acetic anhydride having reduced iodide contamination is separated as a vapour fraction from a liquid fraction, (9) recycling liquid fraction from (8) as wash liquid to the scrubbing section of the preliminary flash vapouriser,

(10) separating by distillation acetic acid from acetic anhydride, in the vapour fraction from (8)

(11) recycling at leas part of the acetic acid separated in (10) to the esterification step (1), and

(12) recovering acetic anhydride and any acetic acid not recycled to the esterification step from the vapour fraction from (8).

In a modification of this embodiment, the post-flash vapouriser may be integral with the fractional distillation column used to effect the fractional distillation of step (6) so that steps (6) to (9) are modified to: (6') separating the volatile fraction from (4) by fractional distillation in a distillation column into an overhead fraction comprising unreacted carbonylation feedstock and iodine-containing promoter, a base vapour fraction comprising carboxylic acid and/or anhydride having reduced iodide contamination and a liquid base fraction, (7') recycling the overhead fraction from (40 ) to the carbonylation step, (8') withdrawing the base vapour fraction from the base of the distillation column and the base liquid fraction from the base of the distillation column, (9') recycling the base liquid fraction from (8') as wash liquid to the scrubbing section of the preliminary flash vapouriser.

As previously discussed the base vapour fraction may be removed from the distillation column t about one or two trays from the base to reduce entrainment.

Details of preferred reactants, reaction conditions and procedures for effecting this particularly preferred embodiment may be found in the previously referred to EP-A-0087870.

Figure 2:
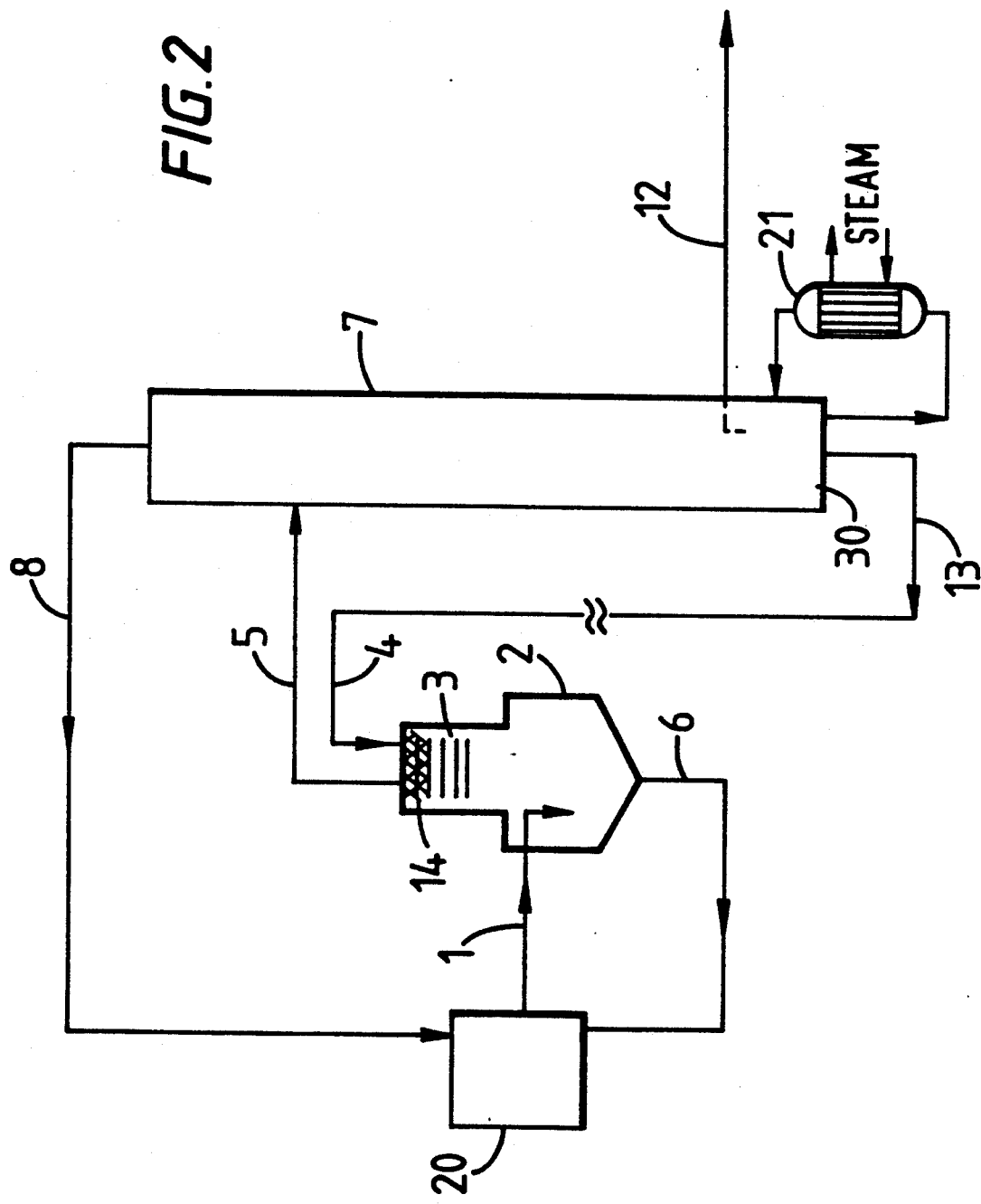

A particularly preferred embodiment of the process of the invention is further illustrated with reference to the accompanying drawings in which FIG. 1 is a simplified flow diagram of the relevant part of a process for the manufacture of acetic anhydride and acetic acid from methanol and carbon monoxide by the integrated esterification, carbonylation and separation steps of EP-A-0087870 and FIG. 2 is a modification of the apparatus of FIG. 1 with the vapouriser being integral with the distillation column.

Referring to FIG. 1 in use the product of the carbonylation reaction consisting of predominantly acetic anhydride, acetic acid, unreacted methyl acetate, rhodium carbonylation catalyst, some methyl iodide promoter and optional co-promoter such as N,N'dimethyl imidazolium iodide is passed from the carbonylation reactor 20 by line 1 to the preliminary flash vapouriser 2 which is equipped with scrubbing trays 3 and an inlet for recycle liquid 4. It also contains knitmesh packing 14. A vapour fraction consisting of acetic anhydride, acetic acid, unreacted methyl acetate and methyl iodide promoter is removed from the preliminary flash vapouriser via line 5 and a liquid fraction comprising involatile carbonylation catalyst and optional co-promoter is removed via line 6 and recycled to the carbonylation reactor 20. The scrubbing trays 3, knitmesh packing 14 and wash liquid 4 therefore are intended to facilitate the removal of involatile iodides in the liquid fraction removed through line 6.

The vapour fraction from the preliminary flash vapouriser 2 is fed via line 5 to the distillation column 7 from which there is removed overhead via line 8 a fraction principally containing unreacted methyl acetate reactant and methyl iodide promoter, which is recycled to the carbonylation reaction and from the kettle 9 via line 10 a base liquid reaction of predominantly iodide-contaminated acetic anhydride and acetic acid.

The base fraction from the distillation column 7 is fed via line 10 to the past-flash vapouriser 11. The post-flash vapouriser is heated by means of an external thermosyphon reboiler (21) with medium pressure steam shellside. From 11 via line 12 is taken a vapour fraction of acetic anhydride and acetic acid having a substantially reduced iodide content. A liquid bleed is taken from the vapouriser via line 13 and recycled as wash liquid to the trays 3 of the preliminary flash vapouriser 2 via the inlet line 4.

The vapour fraction from 11 is separated by distillation into acetic anhydride and acetic acid in a distillation column (not shown), and the acetic acid recycled in the manner described in EP-A-0087870, part of the separated acetic acid being used to produce methyl acetate feed for the reactor by esterification.

FIG. 2 shows a modification of the apparatus of FIG. 1 in that the post flash vapouriser is integral with the distillation column, the remaining apparatus being the same.

Thus in use, the product of the carbonylation reaction consisting of predominantly acetic anhydride, acetic acid, unreacted methyl acetate, rhodium carbonylation catalyst, some methyl iodide promoter and optional co-promoter such as N,N'dimethyl imidazolium iodide is passed from the carbonylation reactor 20 by line 1 to the preliminary flash vapouriser 2 which is equipped with scrubbing trays 3 and an inlet for recycle liquid 4. It also contains knitmesh packing 14. A vapour fraction consisting of acetic anhydride, acetic acid, unreacted methyl acetate and methyl iodide promoter is removed from the preliminary flash vapouriser via line 5 and a liquid fraction comprising involatile carbonylation catalyst and optional co-promoter is removed via line 6 and recycled to the carbonylation reactor 20. The scrubbing trays 3, knitmesh packing 14 and wash liquid 4 therefore are intended to facilitate the removal of involatile iodides in the vapour fraction removed through line 6.

The vapour fraction from the flash vapouriser 2 is fed via line 5 to the distillation column 7 from which is removed overhead via line 8 in fraction principally containing unreacted methyl acetate reactant and methyl iodide promoter, which is recycled to the carbonylation reaction.

In FIG. 2 the post-flash vapouriser is integral with the distillation column so that the kettle 30 of the distillation column 7 acts as the vessel of the post-flash vapouriser and vapourisation is effected by means of an external thermosyphon reboiler 21 with medium pressure steam shell-side which also boils the distillation column contents.

From the distillation column kettle 30 there is taken via line 12 a vapour base fraction of acetic anhydride and acetic acid having a substantially reduced iodide content than if a liquid fraction were taken from the base of the distillation column. A liquid bleed fraction is taken from the kettle 30 via line 13 and recycled as wash liquid to the trays 3 of the preliminary flash vapouriser 2 via inlet 4. The vapour fraction may also be removed about one or two trays from the base of the distillation column.

The vapour fraction removed from 30 through line 12 is separated by distillation into acetic anhydride acetic acid in a distillation column (not shown), and the acetic acid recycled in the manner described in EP-A-0,087,870 part of the separated acetic acid being used to produce methyl acetate for the reactor by esterification.

The invention will now be illustrated by reference to the following Examples.

EXAMPLES 1 AND 2

Apparatus similar to that illustrated in FIG. 1 was used for these Examples.

Liquid composition from a rhodium-catalysed carbonylation of methanol/methyl acetate/water in the presence of methyl iodide promoter and N,N'dimethyl imidazolium iodide co-promoter in a continuous, stirred reactor was passed to a preliminary flash vapouriser. A liquid fraction comprising involatile rhodium carbonylation catalyst and N,N'dimethyl imidazolium iodide was recycled from the preliminary flash vapouriser to the carbonylation reactor. The vapour fraction from the preliminary flash vapouriser was passed to a distillation column. From the head of the distillation column a fraction comprising methyl acetate reactant and methyl iodide promoter was recycled to the carbonylation reactor. A liquid fraction was taken from the base of the distillation column, cooled and collected in a tank before being passed to a steam-heated vapouriser operating at 1 barg pressure and about 149° C. The compositions of the feed, vapour faction and liquid fractions are shown in Tables 1 and 2 for Examples 1 and 2.

From the results in Tables 1 and 2 it is clear that the vapour fraction has a significantly reduced iodide contamination than the feed despite the feed having already been subjected to a preliminary flash.

TABLE 1

EXAMPLE 1

| STREAM | FEED | VAPOUR FRACTION | LIQUID FRACTION |
|---|---|---|---|
| Flow rate (l/hr) | 9.3 | 8.3 | 1.0 |
| Composition (by weight) | | | |
| Acetic acid (%) | 71.0 | 69.1 | 58.1 |
| Acetic anhydride (%) | 27.8 | 29.4 | 37.8 |
| Iodide (ppm) | 37 | 5.6 | 307 |

TABLE 2

EXAMPLE 2

| STREAM | FEED | VAPOUR FRACTION | LIQUID FRACTION |
|---|---|---|---|
| Flow rate (l/hr) | 9.4 | 8.4 | 1.0 |
| Composition (by weight) | | | |
| Acetic acid (%) | 67.6 | 66.6 | 56.8 |
| Acetic anhydride (%) | 27.4 | 29.4 | 39.3 |
| Iodide (ppm) | 44.8 | 5.4 | 360 |

EXAMPLES 3 AND 4

Apparatus similar to that illustrated in FIG. 2 was used for these Examples.

Liquid composition from a rhodium-catalysed carbonylation of methanol/methyl acetate/water in the presence of methyl iodide promoter and N,N'dimethyl imidazolium iodide co-promoter in a continuous, stirred reactor was passed to a preliminary flash vapouriser. A liquid fraction comprising involatile rhodium carbonylation catalyst and N,N'dimethyl imidazolium-iodide was recycled from the preliminary flash vapouriser to the carbonylation reactor. The vapour fraction from the preliminary flash vapouriser was passed to a 3 inch diameter Oldershaw distillation column operated at atmospheric pressure. From the head of the distillation column a fraction comprising methyl acetate reactant and methyl iodide promoter was recycled to the carbonylation reactor. A vapour fraction comprising acetic acid and acetic anhydride low in iodide contamination was taken from tray 2 of the distillation column counting from the base. A base liquid bleed fraction was taken from the base of the distillation column and recycled to the preliminary flash vapouriser. In Example 3, the distillation column was operated with a return of reflux to the head of the column at a reflux: heads take off ratio of 1,94 to 1.0, the reflux ratio was unrecorded in Example 4.

Two Experiments were performed and the results are shown in Tables 3 and 4. The low iodide contents of the vapour fraction streams and the high iodide content of the based bleed fractions indicate that the vapour fractions have lower iodide contents than if the acid/anhydride process streams were taken as liquid from the base of the distillation column.

TABLE 3

EXAMPLE 3
Average column base temperature 132.1° C.;
head temperature 72.4° C.

| STREAM | VAPOUR FRACTION | LIQUID BASE BLEED |
|---|---|---|
| Flow rate (g/hr) | 1876.6 | 325 |
| Composition (by weight) | | |
| Acetic acid (%) | 56.6 | 29.8 |
| Acetic anhydride (%) | 43.0 | 67.8 |

TABLE 3-continued

EXAMPLE 3
Average column base temperature 132.1° C.;
head temperature 72.4° C.

| STREAM | VAPOUR FRACTION | LIQUID BASE BLEED |
|---|---|---|
| Iodide (ppm) | 1.3 | 100 |

TABLE 4

EXAMPLE 4
Average column base temperature 131.9° C.;
head temperature 71.3° C.

| STREAM | VAPOUR FRACTION | LIQUID BASE BLEED |
|---|---|---|
| Flow rate (g/hr) | 1366.8 | 196.9 |
| Composition (by weight) | | |
| Acetic acid (%) | 58.5 | 30.2 |
| Acetic anhydride (%) | 41.2 | 67.2 |
| Iodide (ppm) | 4.0 | 230 |

I claim:

1. A process for purifying an iodide-contaminated carboxylic acid and/or anhydride fraction obtained by liquid phase carbonylation of a carbonylatable feedstock using a carbonylation catalyst, and an iodine-containing promoter and freed from carbonylation catalyst, carbonylation feedstock and iodine-containing promoter components in which process the iodide-contaminated carboxylic acid and/or anhydride fraction is fed to a vapouriser hereinafter referred to as the post-flash vapouriser, wherein carboxylic acid and/or anhydride having a reduced iodide contamination is separated as a vapour fraction from a liquid fraction.

2. A process as claimed in claim 1 in which the carboxylic acid and/or anhydride is obtained by liquid phase carbonylation of a carbonylatable feedstock using a carbonylation catalyst, an iodine-containing promoter and an iodine-containing co-promoter and said fraction is freed from said carbonylation catalyst, carbonylation feedstock, iodine-containing promoter and iodine-containing co-promoter components before being fed to said post-flash vapouriser.

3. A process as claimed in claim 1 or claims 2 in which the carboxylic acid and/or anhydride is freed from carbonylation catalyst, carbonylation feedstock and iodine-containing promoter and iodine-containing co-promoter, if present, by feeding liquid phase carbonylation product to a preliminary flash vapouriser wherein a liquid fraction comprising carbonylation catalyst and iodine-containing co-promoter, if present, is separated from a vapour fraction comprising carboxylic acid and/or anhydride, carbonylation feedstock and iodine-containing promoter components, the liquid fraction being recycled to the carbonylation reactor and the vapour fraction being passed to a distillation column wherein an overhead fraction comprising carbonylation feedstock and iodine-containing promoter is separated from a bottoms fraction comprising iodide-contaminated carboxylic acid and/or anhydride which bottoms fraction is fed to the post-flash vapouriser wherein carboxylic acid and/or anhydride having a reduce iodide contamination is separated as a vapour fraction from a liquid fraction.

4. A process as claimed in claim 3 in which the post-flash vapouriser is a flash vapouriser.

5. A process as claimed in claim 3 modified in that the post-flash vapouriser is integral with the distillation column and the vapour fraction from the preliminary flash vapouriser is passed to the distillation column wherein an overhead fraction comprising carbonylation feedstock and iodine-containing promoter is removed from the distillation column and a vapour fraction comprising carboxylic acid and/or anhydide is taken from the base of the distillation column separately from a liquid base fraction which is removed from the base of the distillation column.

6. A process as claimed in claim 1 in which the post-flash vapouriser is operated at a pressure of up to 10 barg and/or a temperature in the range 100° to 200° C.

7. A process as claimed in claim 3 in which the preliminary flash vapouriser is provided in the upper region thereof with a scrubbing section to which is provided a liquid as wash therefore.

8. A process as claimed in claim 1 in which there is purified a carboxylic acid having from 2 to 4 carbon atoms and/or an anhydride thereof.

9. A process as claimed in claim 8 in which there is purified a fraction comprising acetic acid and acetic anhydride.

10. A process as claimed in claim 9 in which said acetic acid and acetic anhydride are produced by the carbonylation of carbonylatable feedstock in the presence of a rhodium carbonylation catalyst, methyl iodide promoter and N,N′dimethyl imidazolium iodide co-promoter.

11. A process for the production of acetic anhydride with or without net co-production of acetic acid from methanol and carbon monoxide in a series of esterification, carbonylation and separation steps comprising:
   (1) reacting methanol with recycle acetic acid in an esterification step to form an esterification product containing predominantly methyl acetate, water and optionally unreacted methanol,
   (2) removing part of the water from the esterification product,
   (3) reacting the esterification product still containing water as carbonylatable feedstock with carbon monoxide in a carbonylation step in the presence as catalyst of free or combined metallic carbonylation catalyst, an iodine-containing promoter and optionally an iodine-containing co-promoter to form a carbonylation product containing acetic acid and acetic anhydride,
   (4) feeding the carbonylation product to a preliminary flash vapouriser provided in the upper region thereof with a scrubbing section wherein a liquid fraction comprising carbonylation catalyst and optional iodine-containing co-promoter is separated from a vapour fraction comprising acetic acid, acetic anhydride, carbonylation feedstock and iodine-containing promoter,
   (5) recycling liquid fraction from (4) to the carbonylation step,
   (6) separating the vapour fraction from (4) by fractional distillation in a distillation column into a base fraction comprising iodide-contaminated acetic acid and acetic anhydride and an overhead fraction comprising unreacted carbonylation feedstock and iodine-containing promoter,
   (7) recycling the overhead fraction from (6) to the carbonylation step,
   (8) feeding the base fraction from (6) comprising iodide-contaminated acetic acid and acetic anhydride to a post-flash vapouriser wherein acetic acid and acetic anhydride having reduced iodide contamination is separated as a vapour fraction from a liquid fraction,
   (9) recycling liquid fraction from (8) as wash liquid to the scrubbing section of the preliminary flash vapouriser,
   (10l) separating by distillation acetic acid from acetic anhydride, in the vapour fraction from (8)
   (11) recycling at least part of the acetic acid separated in (10) to the esterification step (1), and
   (12) recovering acetic anhydride and any acetic acid not recycled to the esterification step from the vapour fraction from (8).

* * * * *

UNITED STATES PATENT AND TRADEMARK OFFICE
CERTIFICATE OF CORRECTION

PATENT NO. : 5,227,520
DATED : July 13, 1993
INVENTOR(S) : Jeremy B. Cooper

It is certified that error appears in the above-indentified patent and that said Letters Patent is hereby corrected as shown below:

On the Title Page, Item [54], correct the spelling of the word "ANYHYDRIDE".

Column 2, line 6, the patent number should read "5,003,104"
Column 3, line 19, there should be a comma (,) after "methanol,"
Column 4, line 8, correct the spelling of the word "using"
Column 4, lines 20-22, should connect as a single sentence
Column 4, line 56, "by freed" should reab "be freed"
Column 4, line 63, correct the spelling of the word "feedstock"
Column 6, line 41, correct the spelling of the word "least"
Column 6, line 65, "t" should read "column at about"
Column 7, line 5, "in which" should read "in which Fig. 1 is"
Column 7, line 10, should read "separation steps of EP-A-0087870 and Fig. 2 is a""
Column 10, line 63, correct the spelling of the word "reduced"

Signed and Sealed this

Tenth Day of May, 1994

Attest:

BRUCE LEHMAN

Attesting Officer     Commissioner of Patents and Trademarks